(12) United States Patent
Burg et al.

(10) Patent No.: US 7,128,913 B2
(45) Date of Patent: Oct. 31, 2006

(54) ERYTHROPOIETIN CONJUGATES

(75) Inventors: Josef Burg, Weilheim (DE); Alfred Engel, Tutzing (DE); Reinhard Franze, Penzberg (DE); Bernd Hilger, Penzberg (DE); Hartmut Ernst Schurig, Munich (DE); Wilhelm Tischer, Peissenberg (DE); Manfred Wozny, Weilheim (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 481 days.

(21) Appl. No.: 10/014,363

(22) Filed: Dec. 11, 2001

(65) Prior Publication Data

US 2002/0115833 A1 Aug. 22, 2002

(30) Foreign Application Priority Data

Dec. 20, 2000 (EP) .................................. 00127891

(51) Int. Cl.
*A61K 39/385* (2006.01)
*C07K 1/00* (2006.01)
*A61K 35/14* (2006.01)

(52) U.S. Cl. ................. 424/195.11; 530/397; 530/350; 514/2; 514/8; 424/194.1; 930/10; 930/90

(58) Field of Classification Search ................ 530/397, 530/350; 514/2, 8; 424/194.1, 195.11; 930/10, 930/90
See application file for complete search history.

(56) References Cited

U.S. PATENT DOCUMENTS

| | | | |
|---|---|---|---|
| 5,272,071 | A | 12/1993 | Chappel |
| 5,547,933 | A | 8/1996 | Lin |
| 5,621,080 | A | 4/1997 | Lin |
| 5,641,670 | A | 6/1997 | Treco et al. |
| 5,672,662 | A | 9/1997 | Hedgepeth et al. |
| 5,733,761 | A | 3/1998 | Treco et al. |
| 5,981,214 | A | 11/1999 | Skoultchi |
| 6,340,742 | B1 | 1/2002 | Burg et al. |
| 6,583,272 | B1 * | 6/2003 | Bailon ........................ 530/397 |

FOREIGN PATENT DOCUMENTS

| | | |
|---|---|---|
| EP | 0 148 605 B2 | 7/1985 |
| EP | 0 205 564 B1 | 12/1986 |
| EP | 0 209 539 B1 | 1/1987 |
| EP | 0 267 678 A1 | 5/1988 |
| EP | 0 307 247 B1 | 3/1989 |
| EP | 0 343 635 B1 | 11/1989 |
| EP | 0 481 791 A2 | 4/1992 |
| EP | 0 513 738 A2 | 11/1992 |
| EP | 0 605 963 A2 | 7/1994 |
| EP | 0 640 619 A1 | 3/1995 |
| EP | 0 248 656 B1 | 12/1997 |
| EP | 1 064 951 | 1/2001 |
| WO | WO 88/00967 | 2/1988 |
| WO | WO 90/11354 | 10/1990 |
| WO | WO 94/01451 | 1/1994 |
| WO | WO 96/11953 A1 | 4/1996 |
| WO | WO 96/35718 | 11/1996 |
| WO | WO 96/41813 | 12/1996 |
| WO | WO 97 03106 | 1/1997 |
| WO | WO 97/09996 | 3/1997 |
| WO | WO 97/40850 | 11/1997 |
| WO | WO 98 32466 | 7/1998 |
| WO | WO 98/05363 | 12/1998 |
| WO | WO 98/58660 | 12/1998 |
| WO | 99/07735 * | 2/1999 |
| WO | WO 99/07401 | 2/1999 |
| WO | WO 00 32772 | 6/2000 |
| WO | WO 0042175 | 7/2000 |
| WO | WO 01 02017 | 1/2001 |
| WO | WO 01 87329 | 11/2001 |

OTHER PUBLICATIONS

Bill et al. Expression and mutagenesis of recombinant human and murine erythropoietins in *Escherichia coli*. (1995) Biochim. Biophys. Acta. 1261: 35-43.*
Wen et al. Erythropoietin Structure-Function Relationships: High Degree of Sequence Homology Among Mammals. (1993) Blood 82(5): 1507-1516.*
Bavister, B., Exp. Zoology vol. 271 (1981) pp. 45-51.
Dalbey, R.E. et al., Protein Sci. vol. 6, pp. 1129-1138.
Danna, R. P., Rudnick, S. A., Abels, R. I., In: MB, Garnick, ed. Erythropoietin in Clinical Applications-An International Perspective. New York, NY: Marcel Dekker, 1990, pp. 301-324.
Egrie, J. C., Strickland, T.W., Lane, J. et al. (1986) Immunobiol. vol. 72 pp. 213-224.
Egrie, J. C., Eschbach, J. W., McGuire, T., Adamson, J.W. (1988) Kidney Intl. vol. 33 pp. 262-263.
Erslev, A. J. (1953) Blood vol. 8, pp. 349-357.

(Continued)

*Primary Examiner*—Nashaat T. Nashed
*Assistant Examiner*—Holly Schnizer
(74) *Attorney, Agent, or Firm*—George W. Johnston; Patricia S. Rocha-Tramaloni

(57) ABSTRACT

The present invention refers to conjugates of erythropoietin with poly(ethylene glycol) comprising an erythropoietin glycoprotein having an N-terminal α-amino group and having the in vivo biological activity of causing bone marrow cells to increase production of reticulocytes and red blood cells and selected from the group consisting of human erythropoietin and analogs thereof which have the sequence of human erythropoietin modified by the addition of from 1 to 6 glycosylation sites or a rearrangement of at least one glycosylation site; said glycoprotein being covalently linked to one poly(ethylene glycol) group of the formula

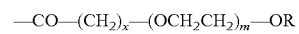

wherein the —CO of the poly(ethylene glycol) group forms an amide bond with said N-terminal α-amino group; and wherein R is lower alkyl; x is 2 or 3; and m is from about 450 to about 1350.

11 Claims, 8 Drawing Sheets

OTHER PUBLICATIONS

Eschbach, J. W., Egri J. C. Downing, M. R. et al., (1987) NEJM vol. 316 pp. 73-78.

Eschbach, J. W., Abdulhadi, M. H. Browne, J. K. et al., (1989) Ann. Intern. Med. vol. 111 pp. 992-1000.

Gaertner, H. F., Offord, R.E., Biconjugates Chem. vol. 7(1) pp. 38-44 (1996).

Huang, Proc. Natl. Acad. Sci. USA (1984) pp. 2708-2712.

Jacobson, L. O. Boldwasser, E., Freid, W. and Plzak, LF (1957) Nature vol. 179 pp. 633-634.

Kawamoto, T. et al, Analytical Biochem. vol. 130 (1983) pp. 445-453.

Kowar, J. and Franek, R., Methods in Enzymology vol. 121 (1986) pp. 277-292.

Krantz, B. S. (1991) Blood vol. 77 pp. 419-434.

Lai, P. H., J. Biol. Chem. vol. 261 (1986) pp. 3116-3121.

Lim, V.S., Degowin, R. L., Zavala, D. et al. (1989) Ann. Intern. Med. vol. 110 pp. 108-114.

Reissmann, K. R. (1950) Blood vol. 5, pp. 372-380.

Sasaki, H., Bothner, B., Dell, A., and Fukuda, M., (1987), J. Biol, Chem., vol. 262 pp. 12059-12076.

Sato, H., Yamamoto, K., Hayashi, E., Takahara, Y., Biconjugates Chem. vol. 11(4) pp. 502-509, 2000.

Zhao, Z. G., Im, J.S. Clarke, D. F. Biconjugates Chem. vol. 10, pp. 424-430 (1999).

US 5,733,746, 03/1998, Treco et al. (withdrawn)

* cited by examiner

```
Ala Pro Pro Arg Leu Ile Cys Asp Ser Arg Val Leu Glu Arg Tyr Leu
 1           5                  10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
        50              55                  60

Gln Gly Leu Ala Leu Leu Ser Glu Ala Val Leu Arg Gly Gln Ala Leu
65                      70                  75                  80

Leu Val Asn Ser Ser Gln Pro Trp Glu Pro Leu Gln Leu His Val Asp
                85                  90                      95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp
                165
```

*FIG. 1*

Ala Pro Pro Arg Leu Ile Cys Asp Ser Arg Val Leu Glu Arg Tyr Leu
1           5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
        50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

*FIG. 2*

```
    GGAATTCACCACCATGGGGGTGCACGAATGTCCTGCCTGGCTGTGGCTTCTCCTGTCCCT
  1 ---------+---------+---------+---------+---------+---------+ 60
    CCTTAAGTGGTGGTACCCCCACGTGCTTACAGGACGGACCGACACCGAAGAGGACAGGGA
                 M  G  V  H  E  C  P  A  W  L  W  L  L  L  S  L  -

GCTGTCGCTCCCTCTGGGCCTCCCAGTCCTGGGCGCCCCCCCCCGAATCGAGGGCCGCGC
 61 ---------+---------+---------+---------+---------+---------+ 120
    CGACAGCGAGGGAGACCCGGAGGGTCAGGACCCGCGGGGGGGGCTTAGCTCCCGGCGCG
     L  S  L  P  L  G  L  P  V  L  G  A  P  P  R  I  E  G  R  A  -

CCCACCACGCCTCATCTGTGACAGCCGAGTCCTGGAGAGGTACCTCTTGGAGGCCAAGGA
121 ---------+---------+---------+---------+---------+---------+ 180
    GGGTGGTGCGGAGTAGACACTGTCGGCTCAGGACCTCTCCATGGAGAACCTCCGGTTCCT
     P  P  R  L  I  C  D  S  R  V  L  E  R  Y  L  L  E  A  K  E  -

GGCCGAGAATATCACGACGGGCTGTGCTGAACACTGCAGCTTGAATGAGAATATCACTGT
181 ---------+---------+---------+---------+---------+---------+ 240
    CCGGCTCTTATAGTGCTGCCCGACACGACTTGTGACGTCGAACTTACTCTTATAGTGACA
     A  E  N  I  T  T  G  C  A  E  H  C  S  L  N  E  N  I  T  V  -

CCCAGACACCAAAGTTAATTTCTATGCCTGGAAGAGGATGGAGGTCGGGCAGCAGGCCGT
241 ---------+---------+---------+---------+---------+---------+ 300
    GGGTCTGTGGTTTCAATTAAAGATACGGACCTTCTCCTACCTCCAGCCCGTCGTCCGGCA
     P  D  T  K  V  N  F  Y  A  W  K  R  M  E  V  G  Q  Q  A  V  -

AGAAGTCTGGCAGGGCCTGGCCCTGCTGTCGGAAGCTGTCCTGCGGGCCAGGCCCTGTT
301 ---------+---------+---------+---------+---------+---------+ 360
    TCTTCAGACCGTCCCGGACCGGGACGACAGCCTTCGACAGGACGCCCCGGTCCGGGACAA
     E  V  W  Q  G  L  A  L  L  S  E  A  V  L  R  G  Q  A  L  L  -

GGTCAACTCTTCCCAGCCGTGGGAGCCCCTGCAGCTGCATGTGGATAAAGCCGTCAGTGG
361 ---------+---------+---------+---------+---------+---------+ 420
    CCAGTTGAGAAGGGTCGGCACCCTCGGGGACGTCGACGTACACCTATTTCGGCAGTCACC
     V  N  S  S  Q  P  W  E  P  L  Q  L  H  V  D  K  A  V  S  G  -

CCTTCGCAGCCTCACCACTCTGCTTCGGGCTCTGGGAGCCCAGAAGGAAGCCATCTCCCC
421 ---------+---------+---------+---------+---------+---------+ 480
    GGAAGCGTCGGAGTGGTGAGACGAAGCCCGAGACCCTCGGGTCTTCCTTCGGTAGAGGGG
```

TCCAGATGCGGCCTCAGCTGCTCCACTCCGAACAATCACTGCTGACACTTTCCGCAAACT
481   ---------+---------+---------+---------+---------+---------+ 540
      AGGTCTACGCCGGAGTCGACGAGGTGAGGCTTGTTAGTGACGACTGTGAAAGGCGTTTGA
            P  D  A  A  S  A  A  P  L  R  T  I  T  A  D  T  F  R  K  L  -

CTTCCGAGTCTACTCCAATTTCCTCCGGGGAAAGCTGAAGCTGTACACAGGGGAGGCCTG
541   ---------+---------+---------+---------+---------+---------+ 600
      GAAGGCTCAGATGAGGTTAAAGGAGGCCCCTTTCGACTTCGACATGTGTCCCCTCCGGAC
         F  R  V  Y  S  N  F  L  R  G  K  L  K  L  Y  T  G  E  A  C  -

CAGGACAGGGGACAGATGACCAGGTCGAC
601   ---------+---------+--------- 629
      GTCCTGTCCCTGTCTACTGGTCCAGCTG
         R  T  G  D  R  *              -
```

*FIG. 3b*

```
     GGAATTCACCACCATGGGGGTGCACGAATGTCCTGCCTGGCTGTGGCTTCTCCTGTCCCT
1    ---------+---------+---------+---------+---------+---------+  60
     CCTTAAGTGGTGGTACCCCCACGTGCTTACAGGACGGACCGACACCGAAGAGGACAGGGA
                 M  G  V  H  E  C  P  A  W  L  W  L  L  L  S  L  -

GCTGTCGCTCCCTCTGGCCTCCCAGTCCTGGGCGCCCCCCCCGCCCCACCACGCCTCAT
61   ---------+---------+---------+---------+---------+---------+ 120
     CGACAGCGAGGGAGACCCGGAGGGTCAGGACCCGCGGGGGGGCGGGGTGGTGCGGAGTA
      L  S  L  P  L  G  L  P  V  L  G  A  P  P  A  P  P  R  L  I  -

CTGTGACAGCCGAGTCCTGGAGAGGTACCTCTTGGAGGCCAAGGAGGCCGAGAATATCAC
121  ---------+---------+---------+---------+---------+---------+ 180
     GACACTGTCGGCTCAGGACCTCTCCATGGAGAACCTCCGGTTCCTCCGGCTCTTATAGTG
        C  D  S  R  V  L  E  R  Y  L  L  E  A  K  E  A  E  N  I  T  -

GACGGGCTGTGCTGAACACTGCAGCTTGAATGAGAATATCACTGTCCCAGACACCAAAGT
181  ---------+---------+---------+---------+---------+---------+ 240
     CTGCCCGACACGACTTGTGACGTCGAACTTACTCTTATAGTGACAGGGTCTGTGGTTTCA
        T  G  C  A  E  H  C  S  L  N  E  N  I  T  V  P  D  T  K  V  -

TAATTTCTATGCCTGGAAGAGGATGGAGGTCGGGCAGCAGGCCGTAGAAGTCTGGCAGGG
241  ---------+---------+---------+---------+---------+---------+ 300
     ATTAAAGATACGGACCTTCTCCTACCTCCAGCCCGTCGTCCGGCATCTTCAGACCGTCCC
        N  F  Y  A  W  K  R  M  E  V  G  Q  Q  A  V  E  V  W  Q  G  -

CCTGGCCCTGCTGTCGGAAGCTGTCCTGCGGGGCCAGGCCCTGTTGGTCAACTCTTCCCA
301  ---------+---------+---------+---------+---------+---------+ 360
     GGACCGGGACGACAGCCTTCGACAGGACGCCCCGGTCCGGGACAACCAGTTGAGAAGGGT
        L  A  L  L  S  E  A  V  L  R  G  Q  A  L  L  V  N  S  S  Q  -

GCCGTGGGAGCCCCTGCAGCTGCATGTGGATAAAGCCGTCAGTGGCCTTCGCAGCCTCAC
361  ---------+---------+---------+---------+---------+---------+ 420
     CGGCACCCTCGGGGACGTCGACGTACACCTATTTCGGCAGTCACCGGAAGCGTCGGAGTG
        P  W  E  P  L  Q  L  H  V  D  K  A  V  S  G  L  R  S  L  T  -

CACTCTGCTTCGGGCTCTGGGAGCCCAGAAGGAAGCCATCTCCCCTCCAGATGCGGCCTC
421  ---------+---------+---------+---------+---------+---------+ 480
     GTGAGACGAAGCCCGAGACCCTCGGGTCTTCCTTCGGTAGAGGGGAGGTCTACGCCGGAG
        T  L  L  R  A  L  G  A  Q  K  E  A  I  S  P  P  D  A  A  S  -
```

*FIG. 4a*

```
     AGCTGCTCCACTCCGAACAATCACTGCTGACACTTTCCGCAAACTCTTCCGAGTCTACTC
481  ---------+---------+---------+---------+---------+---------+ 540
     TCGACGAGGTGAGGCTTGTTAGTGACGACTGTGAAAGGCGTTTGAGAAGGCTCAGATGAG
      A  A  P  L  R  T  I  T  A  D  T  F  R  K  L  F  R  V  Y  S  -

CAATTTCCTCCGGGGAAAGCTGAAGCTGTACACAGGGGAGGCCTGCAGGACAGGGGACAG
541  ---------+---------+---------+---------+---------+---------+ 600
     GTTAAAGGAGGCCCCTTTCGACTTCGACATGTGTCCCCTCCGGACGTCCTGTCCCCTGTC
      N  F  L  R  G  K  L  K  L  Y  T  G  E  A  C  R  T  G  D  R  -

ATGACCAGGTCGAC
601  ---------+---- 614
     TACTGGTCCAGCTG
      *              -
```

*FIG. 4b*

```
     GGAATTCACCACCATGGGGGTGCACGAATGTCCTGCCTGGCTGTGGCTTCTCCTGTCCCT
  1  ---------+---------+---------+---------+---------+---------+ 60
     CCTTAAGTGGTGGTACCCCCACGTGCTTACAGGACGGACCGACACCGAAGAGGACAGGGA
               M  G  V  H  E  C  P  A  W  L  W  L  L  L  S  L  -

GCTGTCGCTCCCTCTGGGCCTCCCAGTCCTGGGCGCCCCCCCCGGCGCCGCCCACTACGC
 61  ---------+---------+---------+---------+---------+---------+ 120
     CGACAGCGAGGGAGACCCGGAGGGTCAGGACCCGCGGGGGGGGCCGCGGCGGGTGATGCG
     L  S  L  P  L  G  L  P  V  L  G  A  P  P  G  A  A  H  Y  A  -

CCCACCACGCCTCATCTGTGACAGCCGAGTCCTGGAGAGGTACCTCTTGGAGGCCAAGGA
121  ---------+---------+---------+---------+---------+---------+ 180
     GGGTGGTGCGGAGTAGACACTGTCGGCTCAGGACCTCTCCATGGAGAACCTCCGGTTCCT
     P  P  R  L  I  C  D  S  R  V  L  E  R  Y  L  L  E  A  K  E  -

GGCCGAGAATATCACGACGGGCTGTGCTGAACACTGCAGCTTGAATGAGAATATCACTGT
181  ---------+---------+---------+---------+---------+---------+ 240
     CCGGCTCTTATAGTGCTGCCCGACACGACTTGTGACGTCGAACTTACTCTTATAGTGACA
     A  E  N  I  T  T  G  C  A  E  H  C  S  L  N  E  N  I  T  V  -

CCCAGACACCAAAGTTAATTTCTATGCCTGGAAGAGGATGGAGGTCGGGCAGCAGGCCGT
241  ---------+---------+---------+---------+---------+---------+ 300
     GGGTCTGTGGTTTCAATTAAAGATACGGACCTTCTCCTACCTCCAGCCCGTCGTCCGGCA
     P  D  T  K  V  N  F  Y  A  W  K  R  M  E  V  G  Q  Q  A  V  -

AGAAGTCTGGCAGGGCCTGGCCCTGCTGTCGGAAGCTGTCCTGCGGGGCCAGGCCCTGTT
301  ---------+---------+---------+---------+---------+---------+ 360
     TCTTCAGACCGTCCCGGACCGGGACGACAGCCTTCGACAGGACGCCCCGGTCCGGGACAA
     E  V  W  Q  G  L  A  L  L  S  E  A  V  L  R  G  Q  A  L  L  -

GGTCAACTCTTCCCAGCCGTGGGAGCCCCTGCAGCTGCATGTGGATAAAGCCGTCAGTGG
361  ---------+---------+---------+---------+---------+---------+ 420
     CCAGTTGAGAAGGGTCGGCACCCTCGGGGACGTCGACGTACACCTATTTCGGCAGTCACC
     V  N  S  S  Q  P  W  E  P  L  Q  L  H  V  D  K  A  V  S  G  -

CCTTCGCAGCCTCACCACTCTGCTTCGGGCTCTGGGAGCCCAGAAGGAAGCCATCTCCCC
421  ---------+---------+---------+---------+---------+---------+ 480
     GGAAGCGTCGGAGTGGTGAGACGAAGCCCGAGACCCTCGGGTCTTCCTTCGGTAGAGGGG
     L  R  S  L  T  T  L  L  R  A  L  G  A  Q  K  E  A  I  S  P  -
```

*FIG. 5a*

```
     TCCAGATGCGGCCTCAGCTGCTCCACTCCGAACAATCACTGCTGACACTTTCCGCAAACT
481  ---------+---------+---------+---------+---------+---------+ 540
     AGGTCTACGCCGGAGTCGACGAGGTGAGGCTTGTTAGTGACGACTGTGAAAGGCGTTTGA
      P  D  A  A  S  A  A  P  L  R  T  I  T  A  D  T  F  R  K  L  -

CTTCCGAGTCTACTCCAATTTCCTCCGGGGAAAGCTGAAGCTGTACACAGGGGAGGCCTG
541  ---------+---------+---------+---------+---------+---------+ 600
     GAAGGCTCAGATGAGGTTAAAGGAGGCCCCTTTCGACTTCGACATGTGTCCCCTCCGGAC
      F  R  V  Y  S  N  F  L  R  G  K  L  K  L  Y  T  G  E  A  C  -

CAGGACAGGGGACAGATGACCAGGTCGAC
601  ---------+---------+--------- 629
     GTCCTGTCCCCTGTCTACTGGTCCAGCTG
      R  T  G  D  R  *              -
```

FIG. 5b

ERYTHROPOIETIN CONJUGATES

SUMMARY OF THE INVENTION

This invention relates to a conjugate comprising an erythropoietin glycoprotein having an N-terminal α-amino group and one poly(ethyleneglycol), said erythropoietin glycoprotein being selected from the group consisting of human erythropoietin, analogs thereof that have from 1 to 6 additional sites for glycosylation, and human erythropoietin having at least one glycosylation site that is rearranged; said glycoprotein being covalently linked to one poly(ethylene glycol) group of the formula

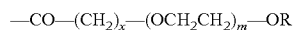

—CO—(CH$_2$)$_x$—(OCH$_2$CH$_2$)$_m$—OR wherein the —CO of the poly(ethylene glycol) group forms an amide bond with the N-terminal α-amino group of the erythropoietin glycoprotein; R is lower alkyl; x is 2 or 3; and m is from about 450 to about 1350.

BACKGROUND OF THE INVENTION

Erythropoiesis is the production of red blood cells which occurs to offset cell destruction. Erythropoiesis is a controlled physiological mechanism that enables sufficient red blood cells to be available for proper tissue oxygenation. Naturally occurring human erythropoietin (EPO) is produced in the kidney and is the humoral plasma factor which stimulates red blood cell production (Carnot, P and Deflandre, C (1906) C.R. Acad. Sci. 143: 432; Erslev, A J (1953 Blood 8: 349; Reissmann, K R (1950) Blood 5: 372; Jacobson, L O, Goldwasser, E, Freid, W and Plzak, L F (1957) Nature 179: 6331–4). Naturally occurring EPO stimulates the division and differentiation of committed erythroid progenitors in the bone marrow and exerts its biological activity by binding to receptors on erythroid precursors (Krantz, B S (1991) Blood 77: 419).

Erythropoietin has been manufactured biosynthetically using recombinant DNA technology (Egrie, J C, Strickland, T W, Lane, J et al. (1986) Immunobiol. 72: 213–224) and is the product of a cloned human EPO gene inserted into and expressed in the ovarian tissue cells of the Chinese hamster (CHO cells). The primary structure of the predominant, fully processed form of human erythropoietin (hEPO) is illustrated in FIG. 1 of Egrie et al. There are two disulfide bridges; between Cys$^7$–Cys$^{161}$ and Cys$^{29}$–Cys$^{33}$. The molecular weight of the polypeptide chain of EPO without the sugar moieties is 18,236 Da. In the intact EPO molecule, approximately 40% of the molecular weight is accounted for by the carbohydrate groups that glycosylate the protein at glycosylation sites on the protein (Sasaki, H, Bothner, B, Dell, A and Fukuda, M (1987) J. Biol. Chem. 262: 12059).

Because human erythropoietin is essential in red blood cell formation, the hormone is useful in the treatment of blood disorders characterised by low or defective red blood cell production. Clinically, EPO is used in the treatment of anemia in chronic renal failure patients (CRF) (Eschbach, J W, Egri, J C, Downing, M R et al. (1987) NEJM 316: 73–78; Eschbach, J W, Abdulhadi, M H, Browne, J K et al. (1989) Ann. Intern. Med. 111: 992; Egrie, J C, Eschbach, J W, McGuire, T, Adamson, J W (1988) Kidney Intl. 33: 262; Lim, V S, Degowin, R L, Zavala, D et al. (1989) Ann. Intern. Med. 110: 108–114) and in AIDS and cancer patients undergoing chemotherapy (Danna, R P, Rudnick, S A, Abels, R I In: M B, Garnick, ed. Erythropoietin in Clinical Applications-An International Perspective. New York, N.Y.: Marcel Dekker; 1990: p. 301–324). However, the bioavailability of commercially available protein therapeutics such as EPO is limited by their short plasma half-life and susceptibility to protease degradation. Several concepts, including pegylated EPO derivatives, have been proposed to overcome these disadvantages.

Common approaches for preparing pegylated proteins yield mixtures of mono- and oligo-pegylated proteins. Moreover, the polyethylene glycol compound (PEG) is bound at several positions of the proteins depending on the amount and reactivities of the available reactive groups on the protein surface. Such a mixture may have severe shortcomings: PEG may be bound at positions which interact with the protein specific receptor and conclusively reduce or even prohibit therapeutic efficacy. To solve this drawback either separation and purification of active ingredients of such a mixture or a selective synthetic route to avoid formation is required. Avoiding formation of any mixtures would greatly simplify the synthesis of a pure active pharmaceutical ingredient in terms of a single positional isomer in essentially higher yields. This is particularly true because separation of positional isomers of PEG-protein mixtures may not be possible using common production scale-synthesis.

Several methods have been proposed for the selective modification of recombinantly produced polypeptides.

European Patent Application EP 651,761 discloses the selective modification of recombinantly produced polypeptides at terminal α-carbon reactive groups. The first step in the method is to form a recombinantly produced polypeptide so that it is protected at the terminal α-carbon reactive group with a biologically added protecting group. The biologically added protecting group is preferably an amino acid, peptide and/or polypeptide that contains at least one site that is cleavable enzymatically or chemically, and preferably has a sequence that is not present in the sequence of the desired polypeptide. Once formed, the biologically protected polypeptide is reacted with chemical protecting agents to protect the side chain groups and then is cleaved with a cleavage reagent specific for the biologically added protecting group. By these means, a polypeptide is produced having an unprotected N-terminal amino group and protected side chain reactive groups. The unprotected N-terminal amino group is modified with a modifying agent to form an N-terminally modified and side-chain-protected polypeptide. It is then deprotected to form an N-terminally modified polypeptide. EP 651,761 suggests that any sequence of amino acids may be attached as biologically added protecting groups. However, in mammalian expression systems, EPO is expressed with a leader signal sequence which is cleaved off by a signal peptidase in order to yield the processed, mature EPO. Such signal peptidases recognise only restricted amino acid residues at the P1' and P3' cleavage site (R. E. Dalbey et al. Protein Sci. 6, 1129 (1997). Thus, a biologically added protecting peptide has to be built up from an N-terminal amino acid sequence of at least three amino acids for cleavage of the signal sequence, followed by an amino acid sequence for enzymatic or chemical removal of the protecting group. If the recognition sequences of both the signal peptidase and the cleavage protease are identical or closely related, then the sequence of the biologically added protecting group can be reduced to a few amino acids.

In another method, N-terminal selective modification is obtained by chemoselective ligation to an aldehyde (or ketone)-functionalized target macromolecule (European Patent Application EP 788,375; Gaertner, H F, Offord, R E, Bioconjugate Chem., 7 (1), 38–44 (1996)). However, this method only works for N-terminal serines or threonines.

In yet another method, selective modification at N-terminal alanine is accomplished by transamination of alanine to pyruvate (European Patent Applications EP 964,702 and EP 605,963). The disadvantage of this method is that the EPO derivative obtained possessed reduced in vitro activity. Also the transformation agents $Cu^{2+}$/glyoxylic acid/NaOAc are likely to produce side reactions within the EPO molecule.

Site specific N-terminal modification was also shown by transglutaminase-mediated incorporation of poly(ethylene glycol) derivatives (Sato, H., Yamamoto, K, Hayashi, E, Takahara, Y, Bioconjugate Chem. 11(4), 502–509 (2000)). But this method showed only low yields and needs incorporation of a peptide tag at the N-terminus and hence modifies the polypeptide structure.

Modification with glyoxylyl-based labelling reagents also enables selective N-terminal modification (Zhao, Z G, Im, J S, Clarke, D F, Bioconjugate Chem. 10, 424–430 (1999)) but is restricted to cysteine.

There exists a need for a pegylated EPO composition that is essentially comprised of a single EPO positional isomer and can readily be synthesized with current state of the art production-scale technology.

BRIEF DESCRIPTION OF THE DRAWINGS

FIG. 1: Shows the primary structure of human EPO (165 amino acids) (SEQ ID NO: 1).

FIG. 2: Shows the primary structure of human EPO (166 amino acids) (SEQ ID NO: 2).

FIG. 3: Shows the primary structure and corresponding nucleic acid sequence (SEQ ID NO: 6)of the APPRIEGR-EPO (SEQ ID NO: 3). The underlined amino acid sequence corresponds to the secretion signal sequence, the wavy line to the amino acid sequence specific for the proteolytic cleavage site.

FIG. 4: Shows the primary structure and corresponding nucleic acid sequence (SEQ ID NO: 7)of APP-EPO (SEQ ID NO: 4). The underlined amino acid sequence corresponds to the secretion signal sequence, the wavy line to the amino acid sequence specific for the proteolytic cleavage site.

FIG. 5: Shows the primary structure and corresponding nucleic acid sequence (SEQ ID NO: 8) of APPGAAHY-EPO (SEQ ID NO: 5). The underlined amino acid sequence corresponds to the secretion signal sequence, the wavy line to the amino acid sequence specific for the proteolytic cleavage site.

DETAILED DESCRIPTION OF THE INVENTION

This invention relates to an erythropoietin conjugate, said conjugate comprising an erythropoietin glycoprotein having an N-terminal α-amino group and having the in vivo biological activity of causing bone marrow cells to increase production of reticulocytes and red blood cells and selected from the group consisting of human erythropoietin and analogs thereof which have the sequence of human erythropoietin modified by the addition of from 1 to 6 glycosylation sites or a rearrangement of at least one glycosylation site; said glycoprotein being covalently linked to one poly(ethylene glycol) group of the formula

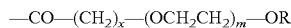

with the —CO of the poly(ethylene glycol) group forming an amide bond with said N-terminal α-amino group; wherein R is lower alkyl; x is 2 or 3; and m is from about 450 to about 1350.

Compared to unmodified EPO (i.e., EPO without a PEG attached) and conventional PEG-EPO conjugates, the present conjugates have an increased circulating half-life and plasma residence time, decreased clearance, and increased clinical activity in vivo. The conjugates of this invention have the same uses as EPO. In particular, the conjugates of this invention are useful to treat patients by stimulating the division and differentiation of committed erythroid progenitors in the bone marrow in the same way EPO is used to treat patients.

This invention also relates to erythropoietin conjugates, comprising an erythropoietin glycoprotein having an N-terminal α-amino group and having the in vivo biological activity of causing bone marrow cells to increase production of reticulocytes and red blood cells and-selected from the group consisting of human erythropoietin and analogs thereof which have sequence of human erythropoietin modified by the addition of from 1 to 6 glycosylation sites or a rearrangement of at least one glycosylation site; said glycoprotein being covalently linked to one poly(ethylene glycol) group of the formula

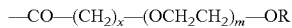

with the —CO—CO (i.e. carbonyl) of the poly(ethylene glycol) group forming an amide bond with said N-terminal α-amino group; wherein R is lower alkyl; x is 2 or 3; and m is from about 450 to about 1350; i.e. m is chosen so that the molecular weight of the conjugate minus the erythropoietin glycoprotein is from about 20 kDa (kilodaltons) to about 60 kDa.

It has been found that the conjugates of this invention can be used in the same manner as unmodified EPO. However, the conjugates of this invention have an increased circulating half-life and plasma residence time, decreased clearance, and increased clinical activity in vivo. Because of these improved properties, the conjugates of this invention can be administered once weekly instead of the three times weekly for unmodified EPO. Decreased frequency of administration is expected to result in improved patient compliance leading to improved treatment outcomes, as well as improved patient quality of life. Compared to conventional conjugates of EPO linked to poly(ethylene glycol) it has been found that conjugates having the molecular weight and linker structure of the conjugates of this invention have an improved potency, stability, area under the curve (AUC), and circulating half-life.

The term "N-terminal α-amino group" refers to the N-terminal amino residue of a peptide, i.e. that end of a peptide or protein chain having an amino acid with a free α-amino ($NH_2$—) group.

The term "erythropoietin" or "EPO" refers to a glycoprotein, having the amino acid sequence set out in FIG. 1 (SEQ ID NO:1) or FIG. 2 (SEQ ID NO:2), preferably in FIG. 1. In one embodiment, this term includes an amino acid sequence substantially homologous to the sequences of FIG. 1 or FIG. 2, whose biological properties relate to the stimulation of red blood cell production and the stimulation of the division and differentiation of committed erythroid progenitors in the bone marrow. As used herein, these terms include such proteins modified deliberately, as for example, by site directed mutagenesis or accidentally through mutations. In an embodiment, the terms erythropoietin or EPO analog include analogs having from 1 to 6 additional sites for glycosylation, analogs having at least one additional amino acid at the carboxy terminal end of the glycoprotein, wherein the additional amino acid includes at least one glycosylation site, and analogs having an amino acid sequence which includes a rearrangement of at least one site for glycosylation. As used herein, "rearrangement" of a glycosylation site means the deletion of one or more glycosylation sites in naturally occurring EPO and the addition of one or more non-naturally occurring glycosylation sites. These terms include both natural and recombinantly produced human erythropoietin.

The term "intermediate EPO" refers to an erythropoietin glycoprotein derivative with a N-terminal extension. Preferably the amino acid extension comprises a secretion signal sequence, optionally followed by a purification tag, e.g. histidine tag (as described for example in H. M. Sassenfeld, Trends in Biotechnol. 8, 88–93 (1990)), followed by an enzyme recognition sequence for digestion of a protein which is followed by the erythropoietin glycoprotein amino acid sequence as defined below.

The term "modified EPO" refers to an intermediate EPO wherein the secretion signal has been cleaved off, e.g. to an EPO glycoprotein which is extended at the N-terminus by a proteolytic cleavage site, e.g. the sequence APPRIEGR, i.e. APPRIEGR-EPO (SEQ ID NO:3), or APP, i.e. APP-EPO (SEQ ID NO: 4), or APPGAAHY, i.e. APPGAAHY-EPO (SEQ ID NO:5) or a sequence substantially homologous thereto (see also FIGS. 3, 4 and 5).

The term "protected modified EPO" refers to a modified EPO, which is obtained by acylation of ε-amino groups with chemical protecting agents, e.g. by citraconylation. The term "protected EPO" means the EPO derivative which is obtained after proteolytic cleavage of the protected modified EPO, i.e. EPO wherein the ε-amino groups have been modified with chemical protecting agents and wherein there is a free N-terminal α-amino group.

The term "homologous amino acid sequence" means that the corresponding amino acid sequences have at least 80% amino acid sequence identity with the corresponding proteolytic cleavage sequences or the corresponding erythropoietin amino acids shown in FIG. 1 or 2 and show the required biological activity (either cleavable by the corresponding protease or having the in vivo biological activity of causing bone marrow cells to increase production of reticulocytes and red blood cells in the case of the pegylated erythropoietin compounds as defined herein. Preferably, the homology is 90%, more preferably 95%.

As used herein, "lower alkyl" means a linear or branched alkyl group having from one to six carbon atoms. Examples of lower alkyl groups include methyl, ethyl and isopropyl. In accordance with this invention, R is any lower alkyl. Conjugates in which R is methyl are preferred.

The erythropoietin conjugates of this invention can be represented by Formula 1:

$$P-NHCO-(CH_2)_x-(OCH_2CH_2)_m-OR \qquad (I)$$

wherein x, m and R are as defined above and P is the residue of an erythropoietin glycoprotein described herein (i.e. without the N-terminal α-amino group which forms an amide linkage with the carbonyl shown in Formula I), having the in vivo biological activity of causing bone marrow cells to increase production of reticulocytes and red blood cells.

In a preferred embodiment of the present invention R is methyl.

Preferably, m is from about 550 to about 1000, more preferably from about 650 to about 750.

In the most preferred embodiment of the present invention R is methyl and m is from about 650 to about 750, which can be represented as follows:

$$CH_3O(CH_2CH_2O)_mCH_2CH_2CH_2CO-NH-P$$

wherein m is from 650 to 750 and P is as defined above. Preferably m has an average of about 730.

Preferably, the glycoprotein of the conjugates as defined above is a human erythropoietin. Human erythropoietin and analogous proteins as defined above can be expressed by endogenous gene activation. Preferred human erythropoietin glycoproteins are those shown in FIG. 1 or 2, most preferably those shown in FIG. 1.

P may be selected from the group consisting of residues of human erythropoietin and analogs thereof having from 1 to 6 additional sites for glycosylation. As set out in detail below, the preparation and purification of EPO are well known in the art. By EPO is meant the natural or recombinant protein, preferably human, as obtained from any conventional source such as tissues, protein synthesis, cell culture with natural or recombinant cells. Any protein having the activity of EPO, such as muteins or otherwise modified proteins, is encompassed. Recombinant EPO may be prepared via expression in CHO, BHK, COS, HeLa or PER.C6 cell lines or other appropriate cell lines of animal or human origin, by recombinant DNA technology or by endogenous gene activation. Expression of proteins, including EPO, by endogenous gene activation is well known in the art and is disclosed, for example in U.S. Pat. Nos. 5,733,761, 5,641,670, 5,733,746, 5,994,122, 5,733,761, 5,641,670, 5,981,214 and 5,272,071, and international patent publication WO 90/11354, the contents of each of which are incorporated herein by reference. The preferred EPO species for the preparation of erythropoietin glycoprotein products are human EPO species. More preferably, the EPO species is the human EPO having the amino acid sequence set out in FIG. 1 or FIG. 2, more preferably the amino acid sequence set out in FIG. 1. In one embodiment, P is the residue of a glycoprotein analog having from 1 to 6 additional sites for glycosylation.

Glycosylation of a protein, with one or more oligosaccharide groups, occurs at specific locations along a polypeptide backbone and greatly affects the physical properties of the protein such as protein stability, secretion, subcellular localisation, and biological activity. Glycosylation is usually of two types. O-linked oligosaccharides are attached to serine or threonine residues and N-linked oligosaccharides are attached to asparagine residues. One type of oligosaccharide found on both N-linked and O-linked oligosaccharides is N-acetylneuraminic acid (sialic acid), which is a family of amino sugars containing 9 or more carbon atoms. Sialic acid is usually the terminal residue on both N-linked and O-linked oligosaccharides and, because it bears a negative charge, confers acidic properties to the glycoprotein. Human erythropoietin, having 165 amino acids, contains three N-linked and one O-linked oligosaccharide chains which comprise about 40% of the total molecular weight of the glycoprotein. N-linked glycosylation occurs at asparagine residues located at positions 24, 38, and 83 and O-linked glycosylation occurs at a serine residue located at position 126. The oligosaccharide chains are modified with terminal sialic acid residues. Enzymatic removal of all sialic acid residues from the glycosylated erythropoietin results in loss of in vivo activity but not in vitro activity because sialylation of erythropoietin prevents its binding, and subsequent clearance, by hepatic binding protein.

The glycoproteins of the present invention include analogs of human erythropoietin with one or more changes in the amino acid sequence of human erythropoietin which result in an increase in the number of sites for sialic acid attachment. These glycoprotein analogs may be generated by site-directed mutagenesis having additions, deletions, or substitutions of amino acid residues that increase or alter sites that are available for glycosylation.

Glycoprotein analogs having levels of sialic acid greater than those found in human erythropoietin are generated by adding glycosylation sites which do not perturb the secondary or tertiary conformation required for biological activity. The glycoproteins of the present invention also include analogs having increased levels of carbohydrate attachment at a glycosylation site which usually involve the substitution of one or more amino acids in close proximity to an N-linked or O-linked site. The glycoproteins of the present invention also include analogs having one or more amino acids extending from the carboxy terminal end of erythropoietin and providing at least one additional carbohydrate site. The glycoproteins of the present invention also include analogs having an amino acid sequence which includes a rearrangement of at least one site for glycosylation. Such a rearrangement of glycosylation site involves the deletion of one or more glycosylation sites in human erythropoietin and the addition of one or more non-naturally occurring glycosylation sites. Increasing the number of carbohydrate chains on erythropoietin, and therefore the number of sialic acids per erythropoietin molecules may confer advantageous properties such as increased solubility, greater resistance to proteolysis, reduced immunogenecity, increased serum half-life, and increased biological activity. Erythropoietin analogs with additional glycosylation sites are disclosed in more detail in European Patent Application 640 619 (Elliot) published Mar. 1, 1995.

In a preferred embodiment, the glycoproteins of the present invention comprise an amino acid sequence which includes at least one additional site for glycosylation such as, but not limited to, erythropoietins comprising the sequence of human erythropoietin modified by a modification selected from the following:

$Asn^{30}Thr^{32}$;
$Asn^{51}Thr^{53}$,
$Asn^{57}Thr^{59}$;
$Asn^{69}$;
$Asn^{69}Thr^{71}$;
$Ser^{68}Asn^{69}Thr^{71}$;
$Val^{87}Asn^{88}Thr^{90}$;
$Ser^{87}Asn^{88}Thr^{90}$;
$Ser^{87}Asn^{88}Gly^{89}Thr^{90}$;
$Ser^{87}Asn^{88}Thr^{90}Thr^{92}$;
$Ser^{87}Asn^{88}Thr^{90}Ala^{162}$;
$Asn^{69}Thr^{71}Ser^{87}Asn^{88}Thr^{90}$;
$Asn^{30}Thr^{32}Val^{87}Asn^{88}Thr^{90}$;
$Asn^{89}Ile^{90}Thr^{91}$;
$Ser^{87}Asn^{89}Ile^{90}Thr^{91}$;
$Asn^{136}Thr^{138}$;
$Asn^{138}Thr^{140}$;
$Thr^{125}$; and
$Pro^{24}Thr^{125}$.

The notation used herein for modification of amino acid sequence means that the position(s) of the corresponding unmodified protein (e.g. hEPO of FIG. 1 and FIG. 2) indicated by the superscripted number(s) is changed to the amino acid(s) that immediately precede the respective superscripted number(s).

The glycoprotein may also be an analog having an amino acid sequence which includes a rearrangement of at least one site for glycosylation. The rearrangement may comprise a deletion of any of the N-linked carbohydrate sites in human erythropoietin and an addition of an N-linked carbohydrate site at position 88 of the amino acid sequence of human erythropoietin. Preferably, the glycoprotein is an analog selected from the group consisting of $Gln^{24}$ $Ser^{87}$ $Asn^{88}$ $Thr^{90}$EPO; $Gln^{38}$ $Ser^{87}$ $Asn^{88}$ $Thr^{90}$ EPO; and $Gln^{83}$ $Ser^{87}$ $Asn^{88}$ $Thr^{90}$ EPO.

The symbol "m" represents the number of ethylene oxide residues ($OCH_2CH_2$) in the poly(ethylene oxide) group. A single PEG subunit of ethylene oxide has a molecular weight of about 44 daltons. Thus, the molecular weight of the conjugate (excluding the molecular weight of the EPO) depends on the number "m". In the conjugates of this invention "m" is from about 450 to about 1350 (corresponding to a molecular weight of about 20 kDa to about 60 kDa), preferably from about 650 to about 750 (corresponding to a molecular weight of about 30 kDa), most preferably about 730. The number m is selected such that the resulting conjugate of this invention has a physiological activity comparable to unmodified EPO, which activity may represent the same as, more than, or a fraction of the corresponding activity of unmodified EPO. A molecular weight of "about" a certain number means that it is within a reasonable range of that number as determined by conventional analytical techniques. The number "m" is selected so that the molecular weight of the poly(ethylene glycol) chain covalently linked to the erythropoietin glycoprotein is from about 20 kDa to about 60 kDa, and is preferably about 32 kDa.

The steps of the method for the preparation of the above compounds involve forming a recombinant single copy erythropoietin glycoprotein or a portion thereof so that the single copy glycoprotein is protected with one or more biologically added protecting groups at the N-terminal α-amino. The recombinant erythropoietin can then be reacted with a protecting agent to selectively protect reactive side chain amino groups and thereby prevent amino side chains groups from being modified with the pegylation reagent. The erythropoietin glycoprotein can be cleaved with at least one cleavage reagent specific for the biological. protecting group to form an unprotected terminal amino acid α-carbon reactive amino group.

The unprotected terminal amino acid α-carbon reactive group may be modified with a pegylation reagent. The side chain protected terminally modified erythropoietin glycoprotein is then deprotected at the side chain groups to form a terminally modified (=pegylated) recombinant erythropoietin glycoprotein.

The invention is also directed to a process of preparing a pegylated EPO conjugate comprising the steps of:
a) expressing and, preferably serum free fermenting, a recombinant EPO protein that has an N-terminal peptidic extension that includes a proteolytic cleavage site,
b) protecting the ε-amino groups,
c) proteolytically cleaving the N-terminal peptidic extension,
d) pegylating the N-terminal α-amino group,
e) deprotecting the ε-amino groups of the erythropoietin glycoprotein, and
f) optionally, following any one or more of step a)–e) above by a purification step.

The invention also relates to the above process wherein the recombinant EPO comprises a sequence selected from the group consisting of the amino acid sequences shown in FIGS. 1 to 5. The ε-amino groups may be protected by a citraconylation and the N-terminal α-amino group may be pegylated with

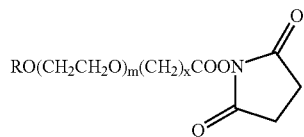

(II)

in which R, m and x are as defined above.

In more detail, the above steps may be performed as follows:

A) Expression, Fermentation and Purification of Modified EPO:

Cloning and expression methods for EPO and EPO-related molecules are known in the art. Human erythropoietin (EPO) is a human glycoprotein which stimulates the formation of erythrocytes. Its preparation and therapeutic application are described in detail for example in U.S. Pat. Nos. 5,547,933 and 5,621,080, EP-B 0 148 605, Huang, S. L., Proc. Natl. Acad. Sci. USA (1984) 2708–2712, EP-B 0 205 564, EP-B 0 209 539 and EP-B 0 411 678 as well as Lai, P. H. et al., J. Biol. Chem. 261 (1986) 3116–3121, an Sasaki, H. et al., J. Biol. Chem. 262 (1987) 12059–12076. Erythropoietin for therapeutic uses maybe produced by recombinant means (EP-B 0 148 605, EP-B 0 209 539 and Egrie, J. C., Strickland, T. W., Lane, J. et al. (1986) Immunobiol. 72: 213–224).

Methods for the expression and preparation of erythropoietin in serum free medium are described for example in WO 96/35718, to Burg published Nov. 14, 1996, and in European Pat. Publication No. 513 738, to Koch published Jun. 12, 1992. In addition to the publications mentioned above, it is known that a serum-free fermentation of recombinant CHO cells which contain an EPO gene can be carried out. Such methods are described for example in EP-A 0 513 738, EP-A 0 267 678 and in a general form by Kawamoto, T. et al., Analytical Biochem. 130 (1983) 445–453, EP-A 0 248 656, Kowar, J. and Franek, F., Methods in Enzymology 421 (1986) 277–292, Bavister, B., Exp. Zoology 271 (1981) 45–51, EP-A 0 481 791, EP-A 0 307 247, EP-A 0 343 635, WO 88/00967.

Purification methods for erythropoietin and derivatives of EPO are also known in the art EP-A 0 267 678 discloses an ion exchange chromatography on S-Sepharose, a preparative reverse phase HPLC on a $C_8$ column and a gel filtration chromatography for the purification of EPO produced in serum-free culture after dialysis. The gel filtration chromatography step can be replaced by ion exchange chromatography on S-Sepharose fast flow. It is also proposed that a dye chromatography on a Blue Trisacryl column be carried out before the ion exchange chromatography.

A process for the purification of recombinant EPO is also described by Nobuo, I. et al., J. Biochem. 107 (1990) 352–359. In the Nobuo process EPO is treated with a solution of Tween® 20, phenylmethylsulfonyl fluoride, ethylmaleimide, pepstatin A, copper sulfate and oxamic acid prior to the purification steps.

It is also known to prepare erythropoietin in a serum free fermentation process (EPOsf). See, e.g. WO 96/35718 (Burg), published November 1996.

B) Reaction with a Protecting Agent to Selectively Protect Reactive Side Chain Amino Groups: Preparation of Protected Modified EPO Suitable chemical protecting agents form bonds at unprotected side chain amines and are less stable than and different from those bonds at the N-terminus. Many such chemical protecting agents are known (see for example European Patent Application EP 651,761). Preferred chemical protecting agents include a cyclic dicarboxylic acid anhydrides like maleic or citraconylic anhydrides.

Citraconylation is the preferred method if the target polypeptide or fusion protein (herein termed modified EPO) properties accept slightly alkaline conditions for protection and acidic conditions for deprotection (Dixon, H B F; Perham, R N: Biochem. J. 109 (2), 312–14 (1968); Atassi, M Z, Habeeb, AFSA: Methods Enzymol. 25(Pt. B), 546 –53 (1972)). Optionally, the protected modified EPO may be purified before performing the next step.

C) Proteolytic Cleavage of Protected Modified EPO: Preparation of Protected EPO

Suitable proteases for cleavage of fusion proteins are described by Carter, P: Site-specific proteolysis of fusion proteins; Protein Purification: From Molecular Mechanisms to Large Scale Processes, ACS, Washington D.C., pp. 181–193 (1990). Such proteases require a narrow specificity to cleave selectively at their recognition sequence and not anywhere in the target protein sequence. Examples are factor Xa which cleaves at IEGR↓ (SEQ ID NO: 9) and enterokinase which cleaves at DDDDK↓ (SEQ ID NO: 10). Moreover enterokinase is reported to cleave DDDDKJ↓AP (SEQ ID NO: 11) which indicates specificity at the P1' and P2' site for interleukins (P. Carter). Enterokinase is, however, not preferred if chemical protecting agents to protect the side chain ε-amino groups of lysines have to be introduced. In such case, the enzyme would no longer work at the wanted cleaving site.

Useful proteases include IgA protease which cleaves preferentially at PP↓XP (X=T, S. A). The XP sequence makes it suitable for interleukins and erythropoietin (EP513073). Another suitable protease is a subtilisin BPN' variant (Genenase™, Genencor Int. Inc.) which cleaves at HY↓.

Optionally the protected EPO protein may be purified at this stage.

D) Modification with a Pegylation Reagent:

Human EPO contains nine free amino groups, the amino-terminal amino group plus the ε-amino groups of 8 lysine residues. When the pegylation reagent is an SBA compound of Formula II, it has been found that at pH 7.5, a protein: PEG ratio of 1:3, and a reaction temperature of from about 20–25° C., a mixture of mono-, di-, and trace amounts of the tri-pegylated species are produced if it is reacted with EPO. The pegylated EPO can be administered as a mixture, or as the cation exchange chromatography separated different pegylated species. By manipulating the reaction conditions (e.g., ratio of reagents, pH, temperature, protein concentration, time of reaction etc.), the relative amounts of the different pegylated species can be varied.

Using the procedures as specified herein for protecting EPO, only the N-terminal α-amino group of the N-terminal alanine of the protected EPO is pegylated. Because all of the ε-amino groups of the lysine side chains are protected, neither di-, nor oligo-pegylated protected EPOs are formed The compound of Formula I can be prepared from the known polymeric material:

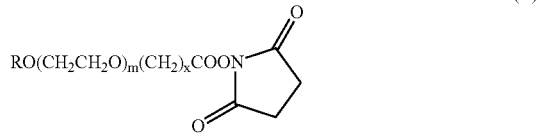

in which R and m are as described above, by condensing the compound of Formula II with the erythropoietin glycoprotein of step C). Compounds of Formula II in which x is 3 are alpha-lower alkoxy, butyric acid succinimidyl esters of poly(ethylene glycol) (lower alkoxy-PEG-SBA). Compounds of Formula II in which x is 2 are alpha-lower alkoxy, propionic acid succinimidyl esters of poly(ethylene glycol) (lower alkoxy-PEG-SPA). Any conventional method of reacting an activated ester with an amine to form an amide can be utilised. In the reaction described above, the exemplified succinimidyl ester is a leaving group causing the amide formation. The use of succinimidyl esters such as the compounds of formula II to produce conjugates with proteins is disclosed in U.S. Pat. No. 5,672,662 (Harris, et al.).

The pegylation reaction may be performed at a molar ratio of 1:5 (EPO to PEG-SBA reagent) up to a final protein concentration of 5 mg/ml. The preferred pegylation reagent is a methoxy-PEG-SBA, which is a compound of Formula II in which R is methyl; x is 3; and m is from about 650 to about 750 (average about 730, corresponding to an average molecular weight of about 32 kDa). Methoxy-PEG-SBA is commercially available from Shearwater Polymers, Inc.

Purification of the reaction product from the reaction mixture may be achieved by conventional chromatographic purification as described in the following Examples.

E) Deprotection of ε-amino groups (Side Chain Amino Groups):

Cleavage of the protection agents may be achieved by conventional methods (see above). In case of decitraconylation, deprotection of the protein may be achieved by stirring the solution at a low pH, e.g. 2.5 for 5 h at ambient temperature. The reaction may be stopped by adjusting the pH to 4.5 with sodium hydroxide and the solution is stored frozen at −20° C. until ready for purification.

The specific activity of EPO or EPO conjugates in accordance with this invention can be determined by various assays known in the art. The biological activity of the purified EPO proteins of this invention are such that administration of the EPO protein by injection to human patients results in bone marrow cells increasing production of reticulocytes and red blood cells compared to non-injected or control groups of subjects. The biological activity of the EPO proteins, or fragments thereof, obtained and purified in accordance with this invention can be tested by methods according to Annable, et al., Bull. Wld. Hlth. Org. (1972) 47: 99–112 and Pharm. Europa Spec. Issue Erythropoietin BRP Bio 1997(2). Another biological assay for determining the activity of EPO protein, the normocythaemic mouse assay, is described in Example 4 below.

The conjugates of this invention can be administered in a therapeutically effective amount to patients in the same way EPO products are currently administered. The therapeutically effective amount is that amount of conjugate necessary for the in vivo biological activity of causing bone marrow cells to increase production of reticulocytes and red blood cells. The exact amount of conjugate is a matter of preference subject to such factors as the exact type of condition being treated, the condition of the patient being treated, as well as the other ingredients in the composition. For example, 0.01 to 10 μg per kg body weight, preferably 0.1 to 3 μg per kg body weight, may be administered e.g. once weekly.

The invention also relates to pharmaceutical compositions comprising a conjugate as described above and a pharmaceutically acceptable excipient and/or carrier.

The pharmaceutical compositions containing the conjugates of the invention may be formulated at a strength effective for administration by various means to a human patient experiencing blood disorders characterised by low or defective red blood cell production. Average therapeutically effective amounts of the conjugate may vary and should be based upon the recommendations and prescription of a qualified physician.

The erythropoietin glycoprotein products prepared in accordance with this invention may be prepared in pharmaceutical compositions suitable for injection with a pharmaceutically acceptable carrier or vehicle by methods known in the art. For example, appropriate compositions have been described in WO97/09996, WO97/40850, WO98/58660, and WO99/07401. The compounds of the present invention may be formulated, for example, in 10 mM sodium/potassium phosphate buffer at pH 7 containing a tonicity agent, e.g. 132 mM sodium chloride. Optionally, the pharmaceutical composition may contain a preservative.

The pharmaceutical compositions of the invention may contain different amounts of erythropoietin, e.g. from about 10 to about 10000 μg/ml, preferably from about 50 μg/ml to about 400 μg/ml.

Preferably, the pharmaceutical compositions comprise a conjugate as defined above, a multiply charged inorganic anion in a pharmaceutically acceptable buffer suitable to keep the solution pH in the range of from about 5.5 to about 7.0, and optionally one or more pharmaceutically acceptable carriers and/or excipients. For example, the composition comprises from about 10 μg to about 10000 μg erythropoietin conjugate per ml, 10–200 mmol/l sulfate, about 10 to about 50 mmol/l phosphate pH 6.0 to 6.5, optionally up to about 1 mM $CaCl_2$, and optionally about 1–5% of a polyol.

An example of a composition according to the invention is:

a) 50 μg/ml or 400 μg/ml erythropoietin conjugate, 10 mM sodium/potassium phosphate, 100 mM NaCl, pH 7.0;

b) 50 μg/ml or 400 μg/ml erythropoietin conjugate, 10 mM sodium phosphate, 120 mM sodium sulfate, pH 6.2;

c) 50 μg/ml or 400 μg/ml erythropoietin conjugate, 10 mM sodium phosphate, 40 mM sodium sulfate, 3% mannitol, pH 6.2;

d) 50 μg/ml or 400 μg/ml erythropoietin conjugate, 10 mM sodium phosphate, 40 mM sodium sulfate, 3% mannitol, 7.5 μM $CaCl_2$, pH 6.2;

e) 50 μg/ml or 400 μg/ml erythropoietin conjugate, 50 mM arginine, 100 mM sodium sulfate, 1 mM $CaCl_2$, pH 6.2; and f) 50 μg/ml or 400 μg/ml erythropoietin conjugate, 50 mM arginine, 30 mM sodium sulfate, 3% mannitol, 1 mM $CaCl_2$, pH 6.2.

Further preferred compositions may comprise from about 10 to about 10000 μg/ml erythropoietin, preferably from about 25 to about 2500 μg/ml erythropoietin, and a) 10 mM sodium/potassium phosphate, 100 mM NaCl, pH 7.0; or b) 10 mM sodium phosphate, 120 mM sodium sulfate, pH 6.2; or c) 10 mM sodium phosphate, 40 mM sodium sulfate, 3% mannitol (w/v), pH 6.2; or d) 10 mM sodium phosphate, 40 mM sodium sulfate, 3% mannitol (w/v), 10 mM methionine, 0.01% pluronic F68 (w/v), pH 6.2; or e) 40 mM arginine, 30 mM sodium sulfate, 3% mannitol (w/v), pH 6.2; or e) 40 mM arginine, 30 mM sodium sulfate, 3% mannitol (w/v), 10 mM methionine, 0.01% pluronic F68 (w/v), pH 6.2.

In the most preferred embodiment, the compositions of the invention comprise an amount erythropoietin protein of 50, 100, 400, 800 or 2500 μg/ml. A most preferred composition also includes 10 mM sodium phosphate, 40 mM sodium sulfate, 3% mannitol (w/v), 10 mM methionine, 0.01% pluronic F68 (w/v), pH 6.2. Another preferred composition, in addition to the EPO conjugate, also includes 40 mM arginine, 30 mM sodium sulfate, 3% mannitol (w/v), 10 mM methionine, 0.01% pluronic F68 (w/v), pH 6.2.

The conjugates of the present invention are especially useful for the preparation of medicaments for the treatment or prophylaxis of diseases correlated with anemia in chronic renal failure patients (CRF), AIDS and for the treatment of cancer patients undergoing chemotherapy.

An additional embodiment of the present invention is a method for the prophylactic and/or therapeutic treatment of disorders involving anemia in chronic renal failure patients (CRF), AIDS and cancer patients undergoing chemotherapy comprising administering to a patient an EPO conjugate as described above.

The invention relates also to compounds as defined above for the treatment of diseases which are associated with anemia in chronic renal failure patients (CRF), AIDS and cancer patients undergoing chemotherapy.

Another aspect of the present invention comprises the above compounds whenever prepared by a process as described above.

A further embodiment of the invention relates to erythropoietin glycoproteins comprising the amino acid sequences as shown in FIG. 1 and FIG. 2 having a N-terminal peptidic extension which represents a proteolytic cleavage site, optionally comprising an N-terminal purification tag. Examples for these peptides are APPRIEGR-EPO (SEQ ID NO: 3), APP-EPO (SEQ ID NO: 4) and APPGAAHY-EPO (SEQ ID NO: 5) (see also FIGS. 3 to 5).

Another embodiment of the invention relates to erythropoietin glycoproteins comprising the amino acid sequences as shown in FIGS. 3 to 5.

The invention will be better understood by reference to the following examples which illustrate but do not limit the invention described herein.

EXAMPLES

Example 1

Expression, Fermentation and Purification of Modified EPO (1) Expression of Modified-EPO Constructs a) Reagents Unless specified, all biochemical reagents used were from Roche Diagnostics GmbH (Mannheim, Germany), and all cell culture reagents from Gibco-BRL (Eggenstein, Germany).

b) Cloning of the wild type EPO expression construct.

For stable expression in Chinese Hamster Ovary (CHO) cells, standard eukaryotic expression vectors such as pcDNA3 (Invitrogen BV, Groningen, Netherlands), pCI-neo (Promega, Madison, Wis., USA) were modified by substituting the neo gene coding for G418-resistance with the gene coding for mice dehydrofolate reductase (DHFR, Crouse et al. J. Biol. Chem. 257, 7887–7897 (1982)), whose expression level is controlled by the simian virus 40 (SV40) early promoter and its late polyadenylation signal. In case of pcDNA3 the resulting vector was designated p. 11381 (M. Tacke et al. Hepatology 26, 1626–1633 (1997)).

The wild type erythropoietin coding fragment was obtained by methods known in the art, e.g. as described by Jacobs K. et al., Nature 313, 806–10 (1985). Preferably, the coding fragment is amplified using primers EPO-EcoRI 5'-GAGCCT<u>GAATTC</u>ACCACC (SEQ ID NO: 12) and EPO-SalI 5'-AGGTGG<u>GTCGAC</u>CTGGTCAT CTGTC-CCCTG (SEQ ID NO: 13). The PCR fragment was digested with EcoRI and SalI (sites are underlined in primer sequences) and cloned into the multiple cloning site of the pre-digested pCI-dhfr vector fragment. Expression of the EPO gene was therefore under control of the human cytomegalovirus (CMV) immediate-early enhancer/promoter region, an optimized chimeric intron for regulated expression and the SV40 late polyadenylation signal.

c) Cloning of APPRIEGR-EPO Expression Construct

The APPRIEGR peptide (residues 28–35 of SEQ ID NO: 3) was assembled as a NarI DNA fragment by two annealed oligonucleotides APPRIEGRfor (residues 28–35 of SEQ ID NO: 3), 5'-<u>CG</u>CCCCCCCCGAATCGAGGGCC<u>G</u> (SEQ ID NO: 14), and APPRIEGRrev (residues 28–35 of SEQ ID NO: 3), 5'-<u>CG</u>CGGCCCTCGATTCGGGGGGG<u>GG</u> (SEQ ID NO: 15) (remnants of NarI site underlined), and cloned in between the N-terminal signal sequence and the mature EPO coding region.

d) Cloning of APP-EPO Expression Construct

The APP peptide was assembled as a NarI DNA fragment by two annealed oligonucleotides APPfor, 5'-<u>CG</u>CCCCCCC, and APPrev, 5'-<u>CG</u>GGGGGG<u>GG</u> (remnants of NarI site underlined), and cloned in between the N-terminal signal sequence and the mature EPO coding region.

e) Cloning of APPGAAHY-EPO Expression Construct

The APPGAAHY peptide (residues 28–35 of SEQ ID NO: 5) was assembled as a NarI DNA fragment by two annealed oligonucleotides APPGAAHYfor (residues 28–35 of SEQ ID NO: 5), 5'-<u>CG</u>CCCCCCCCGGCGCCGCCCACTA (SEQ ID NO: 16), and APPGAAHYrev (residues 28–35 of SEQ ID NO: 5), 5'-<u>CG</u>TAGTGGGCGGCGCCGGGGGG<u>GG</u> (SEQ ID NO: 17) (remnants of NarI site underlined), and cloned in between the N-terminal signal sequence and the mature EPO coding region.

f) Cell Culture Procedures

The mutagenized cell line CHO/dhfr- (ATCC CRL-9096) deficient in the dhfr enzyme gene was obtained from the American Type Tissue Collection (Manassas, Va., USA). Untransfected cells were cultured in α-MEM, 5% dialyzed fetal calf serum (FCS), 2 mM glutamine. Cells were transfected with the EPO plasmids using the FuGENE 6 transfection reagent. Transfected cells were selected in α-MEM lacking nucleosides ((α-MEM), supplemented with 10% dialysed FCS, 2 mM glutamine. Single colonies were isolated by FACS, expanded, and the culture supernatants were assayed for production and secretion of EPO by enzyme linked immunosorbant essay (ELISA). The EPO expression levels were enhanced several times by the amplification of the dhfr and EPO genes in culture media containing increased concentrations of methotrexate (MTX, Sigma Chemical Co., St. Louis, Mo., USA).

(2) Fermentation

In the following the fermentation and purification of a modified EPO is described.

Inoculum Preparation and Fermentation

One vial of the Cell Bank, originating from an modified EPO-producing CHO cell line (Host cell line: ATCC CRL-9096, deficient in the dhfr enzyme gene) was taken from the vapour phase of the liquid nitrogen storage tank. The cells were transferred into glass spinner flasks and cultivated in a hydrogen carbonate-buffered medium in a humidified $CO_2$ incubator. Typical serum free media used for the inocolum preparation and fermentation are disclosed in European Patent Application 513 738, to Koch, published Jun. 12, 1992, or WO 96/35718, to Burg, published Nov. 14, 1996, contain as medium DMEM/F12 (e.g. JRH Biosciences/ Hazleton Biologics, Denver, US, order No. 57-736) and additionally sodium hydrogencarbonate, L+glutamine, D+glucose, recombinant insulin, sodium selenite, diaminobutane, hydrocortisone, iron(II) sulfate, asparagine, aspartic acid, serine and a stabilizer for mammalian cells such as e.g. polyvinyl alcohol, methyl cellulose, polydextran, polyethylene glycol, Pluronic F68, plasma expander polygelin (HEMACCEL®) or polyvinyl pyrrolidone (WO 96/35718).

The cultures were microscopically checked for the absence of contaminating microorganisms, and the cell densities are determined. These tests were performed at each splitting step.

After the initial growth period, the cell culture was diluted with fresh medium to the starting cell density and allowed to undergo another growth cycle. This procedure was repeated until a culture volume of approximately 2 l per glass spinner flask was obtained. After approx. 12 doublings, 1 to 5 liter of this culture was available and was then used as inoculum for the 10 l inoculum fermenter.

After 3–5 days, the culture in the 10 l fermenter was used as inoculum for the 100 l inoculum fermenter.

After 3–5 days of additional cultivation, the culture in the 100 l fermenter was used as inoculum for a 1000 l production fermenter.

Harvesting and Cell Separation

A batch refeed process was used, i.e. when the desired cell density was reached, approx. 80% of the culture was harvested. The remaining culture was replenished with fresh culture medium and cultivated until the next harvest. One production run consisted of a maximum of 10 subsequent harvests: 9 partial harvests and 1 overall harvest at the end of fermentation. Harvesting took place every 3–4 days.

The determined harvest volume was transferred into a cooled vessel. The cells were removed by centrifugation or filtration and discarded. The modified EPO containing supernatant of the centrifugation step was in-line filtered and collected in a second cooled vessel. Each harvest was processed separately during purification. A typical purification of modified EPO-protein is demonstrated below.

(3) Purification of the Modified EPOs

A typical process for the purification of EPO-protein is disclosed in WO 96/35718 (Burg), published Nov. 14, 1996. This purification process is also applicable to the modified EPOs of the current invention as demonstrated below.

(1) Blue Sepharose Chromatography

Blue Sepharose (Pharmacia) consists of Sepharose beads to the surface of which the Cibacron blue dye is covalently bound. Since modified EPO binds more strongly to Blue Sepharose than most non-proteinaceous contaminants and proteinaceous impurities, modified EPO can be enriched in this step. The elution of the Blue Sepharose column was performed by increasing the salt concentration as well as the pH.

The column was filled with Blue Sepharose, regenerated with NaOH and equilibrated with equilibration buffer (sodium/calcium chloride and sodium acetate). The acidified and filtered fermenter supernatant was loaded. After completion of the loading, the column was washed first with a buffer similar to the equilibration buffer containing a higher sodium chloride concentration and consecutively with a Tris-base buffer. The product was eluted with a Tris-base buffer containing 1 M NaCl and collected in a single fraction.

(2) Butyl Toyopearl Chromatography

Butyl Toyopearl 650 C (Toso Haas) is a polystyrene based matrix to which aliphatic butyl-residues are covalently coupled. Since modified EPO binds more strongly to this gel than most of the impurities, it can be eluted with a buffer containing isopropanol. The column was packed with Butyl Toyopearl 650 C, regenerated with NaOH, washed with a Tris-base buffer and equilibrated with a Tris-base buffer containing isopropanol. The Blue Sepharose eluate was adjusted to the concentration of isopropanol in the column equilibration buffer and loaded onto the column. Then the column was washed with equilibration buffer with increased isopropanol concentration. The product was eluted with elution buffer (Tris-base buffer with high isopropanol content) and collected in a single fraction.

(3) Hydroxyapatite Ultrogel Chromatography

Hydroxyapatite Ultrogel™ (Biosepra) consists of hydroxyapatite which is incorporated in an agarose matrix to improve the mechanical properties. Modified EPO has a low affinity to hydroxyapatite and can therefore be eluted at lower phosphate concentrations than protein impurities.

The column was filled with Hydroxyapatite Ultrogel and regenerated with a potassium phosphate/calcium chloride buffer and NaOH followed by a Tris-base buffer. Then it was equilibrated with a Tris-base buffer containing a low amount of isopropanol and sodium chloride.

The modified EPO-containing eluate of the Butyl Toyopearl chromatography was diluted with Tris-base buffer and loaded onto the column. Subsequently the column was washed with equilibration buffer and a Tris-base buffer without isopropanol and sodium chloride. The product was eluted with a Tris-base buffer containing a low concentration of potassium phosphate and collected in a single fraction.

The eluate of the Hydroxyapatite Ultrogel column was concentrated and diafiltered against citraconylation buffer. Concentration/diafiltration was performed with a Millipore Labscale™ TFF System fitted with 10 kDa cut off Millipore Pellicon XL membrane.

Example 2

Citraconylation of Modified EPO, Proteolytic Cleavage and Purification of the Protected EPO The solution of the modified EPO was adjusted to pH 8.5–9.0 and stirred at room temperature. Citraconic anhydride (Merck 8.41321.0100) was added slowly to the stirred solution in aliquots; pH of 9.0 was maintained by addition of 0,5 N NaOH with a pH-stat. The total amount of citraconic anhydride corresponded to a 5-fold molar excess to the ε-amino groups of lysines in the modified EPO. When the addition of citraconic anhydride was complete, the reaction mixture was stirred at room temperature for 1 hour. Residual citraconic anhydride was removed by addition of 2 M ethanolamine solution, adjusted to pH 9.0. Cleavage of the modified protected EPO was achieved by addition of the cleavage protease. In case of the construct as described in Example 1(1c), Factor Xa (Roche Molecular Biochemicals, Order No. 602388) was added to the modified EPO 1:100 (w/w) and stirred at room temperature for several hours. The progress of cleavage was controlled by taking samples and assaying for cleavage products. In case of to low cleavage rate, the amount of the protease can be increased.

When using other proteases, such as IgA protease (prepared as described in EP 513,073) and Genenase™ (Genencor Int. Inc.), the procedure is performed analogously.

The removal of the protease from the reaction mixture was achieved by size exclusion chromatography (SEC) on Superdex™ 75 pg (Pharmacia) or on RP-HPLC.

The Superdex 75 pg material consists of cross-linked agarose and dextran beads. After packing, the column was regenerated with NaOH and equilibrated with a phosphate buffer system with 100 mM sodium chloride.

The reaction mixture from the previous step was concentrated to 10 mg/ml on a Millipore Labscale™ TFF System fitted with 10 kDa cut off Millipore Pellicon XL membrane. About 1–5% of the column volume of this solution was applied to the column in one step. The chromatography was performed in the equilibration buffer system. The product was collected in fractions which were pooled according to their purity as analyzed by analytical rpHPLC.

The pooled fractions were concentrated to 7–8 a Millipore Labscale™ TFF System fitted with 10 kDa cut off Millipore Pellicon XL membrane.

Example 3

Preparation of N-terminally Pegylated EPO

The pegylation reaction was performed at a molar ratio of 1:5 (protected EPO to PEG-SBA reagent) at a final protein concentration of 5 mg/ml. The pegylation reagent used was a methoxy-PEG-SBA, which is a compound of Formula II in which R is methyl; x is 3; and m is from 650 to 750 (average about 730, corresponding to an average molecular weight of about 32 kDa).

The 30 kDa PEG-SBA (Shearwater Polymers, Inc.) was dissolved in 1 mM HCl. Enough 100 mM potassium phosphate buffer, pH 7.5, was added to get a final phosphate concentration of 20 mM in the reaction mixture. Protected EPO (approx. 3 mg/ml in the reaction mixture) was added and the reaction mixture was stirred at ambient temperature (20–25° C.). After 2 h, the reaction was stopped by adjusting the pH to 2.5 with acid.

Decitraconylation of the protein was achieved by stirring the solution at a pH of 2.5 for 5 h at ambient temperature. The reaction was stopped by adjusting the pH to 4.5 with sodium hydroxide and the solution was stored frozen at −20° C. until ready for purification.

The separation of N-terminal pegylated EPO (PEG-A1-EPO) from excess reagents, reaction byproducts and non-pegylated EPO was achieved by chromatography on SP-Sepharose FF (Pharmacia). The SP-Sepharose material consists of sulfopropyl (SP)-groups which are covalently bound to the surface of Sepharose beads. The column was filled with SP-Sepharose and regenerated with phosphoric acid and NaOH and equilibrated with a sodium acetate buffer.

The reaction mixture from the previous step was diluted 1:5 with sodium acetate buffer, pH 3 and applied to the SP-Sepharose column. The column was washed with equilibration buffer to remove excess reagents and reaction byproducts. This was followed by washing with 100 mM NaCl. PEG-A1-EPO was then eluted with 200 mM NaCl. The product was collected in fractions which were pooled according to their purity as determined by high performance Size Exclusion Chromatography. Non-pegylated EPO remaining on the column was eluted with 750 mM NaCl.

The PEG-A1 EPO pool was then concentrated to ~4.5–7.5 mg/ml and diafiltered into the storage buffer, 10 mM potassium phosphate, 100 mM NaCl, pH 7.5.

Concentration/Diafiltration was performed with Millipore Labscale™ TFF System fitted with 10 kDa cut off Millipore Pellicon XL Biomax membrane at ambient temperature. Concentrated PEG-A1 EPO was sterile-filtered and stored frozen at −20° C.

Example 4

In-vivo Activity of PEG-A1-EPO Determined by the Normocythaemic Mouse Assay The normocythaemic mouse bioassay is known in the art (Pharm. Europa Spec. Issue Erythropoietin BRP Bio 1997 (2)). Methods for the monography of erythropoietin of Ph. Eur. BRP are also known. The samples were diluted with BSA-PBS. Normal healthy mice, 7–15 weeks old, were administered s.c. 0.2 ml of the PEG-A1-EPO-solution from Examples 1–3, EPO solution and buffer as control. Over a period of 6 days, blood was drawn by puncture of the tail vein and diluted such that 1 µl of blood was present in 1 ml of an 0.15 µmol acridine orange staining solution. The staining time was 3 to 10 minutes.

The reticulocyte counts were carried out microfluorometrically in a flow cytometer by analysis of the red fluorescence histogram. The reticulocyte counts are given in terms of absolute figures (per 30,000 blood cells analyzed). For the data presented below, each group consisted of 5 mice per day, and the mice were bled only once.

The results of the above experiment are reported in Table 1 below.

The results in Table 1 demonstrate the superior activity and the prolonged half life of PEG-A1-EPO species of the invention as shown by the significantly increased amounts of reticulocytes and the shift of the reticulocytes count maximum using the same dose per mouse (100 ng), compared to EPO derived from CHO cells.

TABLE 1

|       | EPO  | PEG-A1-EPO   | Control Buffer |
|-------|------|--------------|----------------|
| 72 h  | 2404 | 2911         | 857            |
| 96 h  | 1814 | 3713         | 697            |
| 120 h | 901  | not measured | 701            |
| 144 h | 536  | 3424         | 708            |

SEQUENCE LISTING

<160> NUMBER OF SEQ ID NOS: 5

<210> SEQ ID NO 1
<211> LENGTH: 165
<212> TYPE: PRT
<213> ORGANISM: Homo sapiens

<400> SEQUENCE: 1

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
        50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp
                165

<210> SEQ ID NO 2
<211> LENGTH: 166
<212> TYPE: PRT
<213> ORGANISM: Homo sapiens

<400> SEQUENCE: 2

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
        50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
            165

<210> SEQ ID NO 3
<211> LENGTH: 174
<212> TYPE: PRT
<213> ORGANISM: CHO/dhfr-

<400> SEQUENCE: 3

Ala Pro Pro Arg Ile Glu Gly Arg Ala Pro Pro Arg Leu Ile Cys Asp
1               5                   10                  15

Ser Arg Val Leu Glu Arg Tyr Leu Leu Glu Ala Lys Glu Ala Glu Asn
                20                  25                  30

Ile Thr Thr Gly Cys Ala Glu His Cys Ser Leu Asn Glu Asn Ile Thr
            35                  40                  45

Val Pro Asp Thr Lys Val Asn Phe Tyr Ala Trp Lys Arg Met Glu Val
        50                  55                  60

Gly Gln Gln Ala Val Glu Val Trp Gln Gly Leu Ala Leu Leu Ser Glu
65                  70                  75                  80

Ala Val Leu Arg Gly Gln Ala Leu Leu Val Asn Ser Ser Gln Pro Trp
                85                  90                  95

Glu Pro Leu Gln Leu His Val Asp Lys Ala Val Ser Gly Leu Arg Ser
            100                 105                 110

Leu Thr Thr Leu Leu Arg Ala Leu Gly Ala Gln Lys Glu Ala Ile Ser
        115                 120                 125

Pro Pro Asp Ala Ala Ser Ala Ala Pro Leu Arg Thr Ile Thr Ala Asp
    130                 135                 140

Thr Phe Arg Lys Leu Phe Arg Val Tyr Ser Asn Phe Leu Arg Gly Lys
145                 150                 155                 160

Leu Lys Leu Tyr Thr Gly Glu Ala Cys Arg Thr Gly Asp Arg
                165                 170

<210> SEQ ID NO 4
<211> LENGTH: 169
<212> TYPE: PRT
<213> ORGANISM: CHO/dhfr-

<400> SEQUENCE: 4

Ala Pro Pro Ala Pro Pro Arg Leu Ile Cys Asp Ser Arg Val Leu Glu
1               5                   10                  15

Arg Tyr Leu Leu Glu Ala Lys Glu Ala Glu Asn Ile Thr Thr Gly Cys
                20                  25                  30

Ala Glu His Cys Ser Leu Asn Glu Asn Ile Thr Val Pro Asp Thr Lys
            35                  40                  45

Val Asn Phe Tyr Ala Trp Lys Arg Met Glu Val Gly Gln Gln Ala Val
        50                  55                  60

Glu Val Trp Gln Gly Leu Ala Leu Leu Ser Glu Ala Val Leu Arg Gly
65                  70                  75                  80

Gln Ala Leu Leu Val Asn Ser Ser Gln Pro Trp Glu Pro Leu Gln Leu
                85                  90                  95

His Val Asp Lys Ala Val Ser Gly Leu Arg Ser Leu Thr Thr Leu Leu
            100                 105                 110

Arg Ala Leu Gly Ala Gln Lys Glu Ala Ile Ser Pro Pro Asp Ala Ala
        115                 120                 125

```
-continued

Ser Ala Ala Pro Leu Arg Thr Ile Thr Ala Asp Thr Phe Arg Lys Leu
            130                 135                 140

Phe Arg Val Tyr Ser Asn Phe Leu Arg Gly Lys Leu Lys Leu Tyr Thr
145                 150                 155                 160

Gly Glu Ala Cys Arg Thr Gly Asp Arg
                165

<210> SEQ ID NO 5
<211> LENGTH: 174
<212> TYPE: PRT
<213> ORGANISM: CHO/dhfr-

<400> SEQUENCE: 5

Ala Pro Pro Gly Ala Ala His Tyr Ala Pro Arg Leu Ile Cys Asp
1               5                   10                  15

Ser Arg Val Leu Glu Arg Tyr Leu Leu Glu Ala Lys Glu Ala Glu Asn
                20                  25                  30

Ile Thr Thr Gly Cys Ala Glu His Cys Ser Leu Asn Glu Asn Ile Thr
            35                  40                  45

Val Pro Asp Thr Lys Val Asn Phe Tyr Ala Trp Lys Arg Met Glu Val
        50                  55                  60

Gly Gln Gln Ala Val Glu Val Trp Gln Gly Leu Ala Leu Leu Ser Glu
65                  70                  75                  80

Ala Val Leu Arg Gly Gln Ala Leu Leu Val Asn Ser Ser Gln Pro Trp
                85                  90                  95

Glu Pro Leu Gln Leu His Val Asp Lys Ala Val Ser Gly Leu Arg Ser
            100                 105                 110

Leu Thr Thr Leu Leu Arg Ala Leu Gly Ala Gln Lys Glu Ala Ile Ser
        115                 120                 125

Pro Pro Asp Ala Ala Ser Ala Ala Pro Leu Arg Thr Ile Thr Ala Asp
        130                 135                 140

Thr Phe Arg Lys Leu Phe Arg Val Tyr Ser Asn Phe Leu Arg Gly Lys
145                 150                 155                 160

Leu Lys Leu Tyr Thr Gly Glu Ala Cys Arg Thr Gly Asp Arg
                165                 170
```

The invention claimed is:

1. A process of making a conjugate that comprises an erythropoietin glycoprotein having an N-terminal α-amino group and one poly(ethylene glycol), said erythropoietin glycoprotein being selected from the group consisting of human erythropoietin, analogs thereof that have from 1 to 6 additional sites for glycosylation, and human erythropoietin having at least one glycosylation site that is rearranged, and being covalently linked to one poly(ethylene glycol) group of the formula

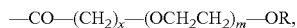

wherein the —CO of the poly(ethylene glycol) group forms an amide bond with the N-terminal α-amino group of the erythropoietin glycoprotein;
R is lower alkyl;
x is 2 or 3; and
m is from about 450 to about 1350;
said process comprising:
 a) expressing and fermenting a recombinant EPO protein that has an N-terminal peptidic extension that includes a proteolytic cleavage sequence,
 b) protecting the ε-amino groups,
 c) proteolytically cleaving the N-terminal peptidic extension,
 d) pegylating the N-terminal α-amino group, and
 e) deprotecting the ε-amino groups of the EPO glycoprotein.

2. The process of claim 1 wherein the fermentation in step a) is serum free.

3. The process of claim 1 wherein any one of steps a)–e) is followed by a purification step.

4. The process of claim 1 wherein the recombinant EPO comprises a sequence selected from the group consisting of the amino acid sequences SEQ ID NO: 1, SEQ ID NO: 2, SEQ ID NO: 3, SEQ ID NO 4: and SEQ ID NO: 5.

5. The process according to claim 1 wherein in step b) the ε-amino groups are protected by citraconylation.

6. The process of claim 1 wherein the N-terminal α-amino group in step d) is pegylated with a group

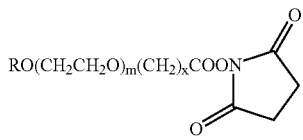

wherein
R is lower alkyl;
x is 2 or 3; and
m is from about 450 to about 1350.

7. The process of claim 6 wherein in the compound of formula II R is methyl, x is 3, m is from about 650 to about 750, and the pegylation reaction in step d) is performed at a molar ratio of 1:5 (protected EPO of step b to reagent of formula II).

8. The process of claim 7 wherein in step b) the ε-amino groups are protected by citraconylation.

9. The process of claim 8, wherein in step e) deprotection of the ε-amino groups is achieved by stirring the product of step d) at a pH of 2.5 for 5 h at ambient temperature.

10. The process of claim 9 wherein step e) is followed by purification step using chromatography.

11. The process of claim 10 wherein the chromatography is carried out on an SP-Sepharose column.

* * * * *